United States Patent
Dong et al.

(10) Patent No.: US 9,995,775 B2
(45) Date of Patent: Jun. 12, 2018

(54) ELECTRICAL IMPEDANCE DETECTING DEVICE OF PORTABLE ELECTRICAL IMPEDANCE IMAGING SYSTEM AND DETECTING METHOD THEREOF

(75) Inventors: Xiuzhen Dong, Xi'an (CN); Xuyang Huo, Xi'an (CN); Fusheng You, Xi'an (CN); Xuetao Shi, Xi'an (CN); Feng Fu, Xi'an (CN); Ruigang Liu, Xi'an (CN); Zhenyu Ji, Xi'an (CN); Canhua Xu, Xi'an (CN); Bin Yang, Xi'an (CN); Min Yang, Xi'an (CN); Jiaxue Qi, Xi'an (CN); Wen Zhang, Xi'an (CN); Nan Wang, Xi'an (CN)

(73) Assignee: FOURTH MILITARY MEDICAL UNIVERSITY, Xi'an, Shaanxi (CN)

( * ) Notice: Subject to any disclaimer, the term of this patent is extended or adjusted under 35 U.S.C. 154(b) by 911 days.

(21) Appl. No.: 13/877,317

(22) PCT Filed: Oct. 13, 2011

(86) PCT No.: PCT/CN2011/080741
§ 371 (c)(1),
(2), (4) Date: Apr. 1, 2013

(87) PCT Pub. No.: WO2013/040817
PCT Pub. Date: Mar. 28, 2013

(65) Prior Publication Data
US 2014/0188417 A1 Jul. 3, 2014

(30) Foreign Application Priority Data
Sep. 23, 2011 (CN) .......................... 2011 1 0286589

(51) Int. Cl.
*G01R 27/02* (2006.01)
*A61B 5/053* (2006.01)
(Continued)

(52) U.S. Cl.
CPC .............. *G01R 27/02* (2013.01); *A61B 5/053* (2013.01); *A61B 5/0536* (2013.01); *A61B 5/7225* (2013.01); *G01R 27/14* (2013.01)

(58) Field of Classification Search
CPC . G40B 30/04; G01S 3/04; G01S 13/06; G01S 13/50; G01S 13/78; H04N 21/4545;
(Continued)

(56) References Cited

U.S. PATENT DOCUMENTS 4,181,134 A * 1/1980 Mason ............... A61B 5/02438
600/502
4,584,885 A * 4/1986 Cadwell ............... G01P 15/131
324/109
(Continued)

FOREIGN PATENT DOCUMENTS

CN 200710075885.1 2/2008
CN 201010162868.3 9/2010
WO 00/28829 5/2000

*Primary Examiner* — Roy Y Yi
*Assistant Examiner* — Jeffrey Aiello

(57) ABSTRACT

A device for detecting electrical impedance by utilizing a theory of excitation and response signals and method thereof, wherein the excitation signal is a square wave excitation current signal (1), the response signal on a target is transformed to a square wave signal with appropriate amplitudes by buffering, amplifying, RC filtering and differential amplifying, then is transformed to a digital signal at a proper time by an analog-to-digital converter. The response signal is sampled once when at high level and once when at low level for every circle by the ADC, and a sample $V_1$ and a sample $V_2$ are obtained respectively, difference of the samples is taken as a detecting result for one circle. An average value of the detecting result from a plurality of circles is taken as a final result. Information of electrical impedance is illustrated by the final result because the excitation current signal is constant.

2 Claims, 1 Drawing Sheet

(51) Int. Cl.
*A61B 5/00* (2006.01)
*G01R 27/14* (2006.01)

(58) Field of Classification Search
CPC .. H04N 21/4725; A61B 5/053; A61B 5/0531; A61B 5/0536; H03F 2200/294; H03F 2200/372
USPC .................................................. 330/253, 254
See application file for complete search history.

(56) References Cited

U.S. PATENT DOCUMENTS

| | | | | |
|---|---|---|---|---|
| 6,529,640 | B1* | 3/2003 | Utagawa | H04N 3/1587 348/234 |
| 6,714,176 | B2* | 3/2004 | Yamamoto | G09G 3/2942 315/169.4 |
| 7,317,465 | B2* | 1/2008 | Allen | G09G 3/007 345/694 |
| 8,508,437 | B2* | 8/2013 | Murata | G09G 3/2927 313/587 |
| 2003/0117345 | A1* | 6/2003 | Yamamoto | G09G 3/2942 345/60 |
| 2004/0012399 | A1* | 1/2004 | Lin | G01N 33/2835 324/698 |
| 2004/0207815 | A1* | 10/2004 | Allen | G09G 3/007 353/31 |
| 2005/0089178 | A1* | 4/2005 | Asada | H03F 3/217 381/106 |
| 2008/0183076 | A1* | 7/2008 | Witte | A61B 5/0093 600/438 |
| 2009/0167324 | A1* | 7/2009 | Prance | G01R 15/165 324/658 |
| 2009/0196522 | A1* | 8/2009 | Hikida | G02B 7/365 382/255 |
| 2009/0212788 | A1* | 8/2009 | Patterson | G01N 15/1031 324/601 |
| 2010/0177084 | A1* | 7/2010 | Murata | G09G 3/2927 345/211 |
| 2011/0068657 | A1* | 3/2011 | Sunaga | H01L 41/042 310/316.01 |
| 2013/0015354 | A1* | 1/2013 | Diamond | G01N 21/4795 250/339.07 |
| 2013/0176039 | A1* | 7/2013 | Lamesch | H03K 17/955 324/683 |
| 2014/0064439 | A1* | 3/2014 | Qing | G11C 19/28 377/75 |
| 2015/0035450 | A1* | 2/2015 | Werner | H05B 33/0815 315/291 |

* cited by examiner

ELECTRICAL IMPEDANCE DETECTING DEVICE OF PORTABLE ELECTRICAL IMPEDANCE IMAGING SYSTEM AND DETECTING METHOD THEREOF

CROSS REFERENCE OF RELATED APPLICATION

This is a U.S. National Stage under 35 U.S.C 371 of the International Application PCT/CN2011/080741, filed Oct. 13, 2011, which claims priority under 35 U.S.C. 119(a-d) to CN 201110286589.2, filed Sep. 23, 2011.

BACKGROUND OF THE PRESENT INVENTION

Field of Invention

The present invention relates to a field of biologic electrical impedance detecting technology, and more particularly to an electrical impedance detecting device of a portable electrical impedance imaging system and a detecting method thereof.

Description of Related Arts

Biologic electrical impedance imaging technology is a tomography technology for displaying the inner structures of organisms by utilizing the information of electrical impedance detected on the body surface without wound. The technology may use an electrical impedance detecting device for detecting electrical impedance of the imaging target to obtain a set of electrical impedance value illustrating the inner information of the imaging target at a certain frequency. A constant excitation current should be applied on the imaging target for detecting the response voltage when detecting electrical impedance, the information of electrical impedance can be obtained by demodulating the response voltage signals.

In a conventional electrical impedance imaging technology, when detecting electrical impedance, excitation sinusoidal current signals are sent to the imaging target, and the response sinusoidal voltage signals are rapidly sampled by high-speed analog-to-digital converter (ADC). Then the information of electrical impedance is obtained by utilizing digital quadrature demodulation for demodulating the response sinusoidal voltage signals.

In a conventional bioelectrical impedance detecting circuit, chips like FPGA and high-speed ADC are needed, and a large number of multiplication operations should be performed when utilizing digital quadrature demodulation. All these lead to complex calculation in CPU and high power consumption. Thus, the conventional electrical impedance imaging technology is not adaptable to being used in a portable electrical impedance imaging system powered by battery.

Therefore, a method with simple structure, simple calculation and low power consumption for detecting bioelectrical impedance is needed to meet the requirements that a portable electrical impedance imaging system should be small in size and low in power consumption.

SUMMARY OF THE PRESENT INVENTION

An object of the present invention is to provide a portable electrical impedance imaging system with battery power resource, simple structure and low power consumption and a method thereof.

Accordingly, in order to accomplish the above objects, the present invention provides an electrical impedance detecting device comprising a pair of exciting electrodes applied on a surface of an imaging target for sending a square wave excitation current signal, a first operational amplifier and a second operational amplifier connected to output ports of the pair of exciting electrodes, a first high-pass filter RC circuit connected to an output port of the first operational amplifier and a second high-pass filter RC circuit connected to an output port of the second operational amplifier, An A/D circuit connected to a signal output port of the first high-pass filter RC circuit and a signal output port of the second high-pass filter RC circuit respectively through a differential amplifier circuit.

The present invention also provides a method for detecting electrical impedance, comprising steps of:

a) sending a square wave excitation current signal to an imaging target through a pair of exciting electrodes for generating a response voltage signal;

b) buffering and amplifying the sampled response voltage signal by a pair of operational amplifiers with high input impedance for neutralizing an impedance influence caused by contact between the electrodes and skins;

c) driving the buffered and amplified response voltage signal through a high-pass filter RC circuit by the operational amplifiers for filtering out a disturbance caused by power frequency and polarized voltage of the electrodes;

d) driving the filtered response voltage signal through a differential amplifier circuit for transforming the filtered response voltage signal to a signal-ended signal and amplifying the single-ended signal; and e) transforming the amplified single-ended signal to a digital signal by an A/D circuit with high-speed and high accuracy for calculating and obtaining information of the electrical impedance by demodulating;

wherein the response voltage signal is sampled once when the response voltage signal is at high level and once when the response voltage signal is at low level for each circle, and a first sample $V_1$ and a second sample $V_2$ are obtained respectively;

a period of respective sampling at high level is supposed as $$t_{p1} = \frac{t_1}{T/2},$$

wherein $t_1$ is a period between a time of respective sampling at high level and a time of a nearest rising edge of the square wave excitation current signal; correspondingly, a period of respective sampling at low level is $$t_{p2} = \frac{t_2}{T/2};$$

wherein $t_{p1}=t_{p2}$;

obtaining information of the electrical impedance by calculating and demodulating difference $V_z=V_1-V_2$ between the first sample $V_1$ and the second sample $V_2$;

taking an average value of $V_z$ from a plurality of circles as a final result.

An excitation signal of the present invention is the square wave excitation current signal, the response voltage signal is buffered by a operational amplifier for neutralizing an impedance influence caused by contact between the electrodes and skins; filtered by a high-pass filter RC circuit for filtering out a disturbance caused by polarized voltage of the electrodes; amplified by a differential amplifier circuit; and transformed to a digital signal by an analog-to-digital converter (ADC) with high-speed, high resolution and high accuracy for obtaining information of the electrical impedance by demodulating.

The response voltage signal is sampled once when the response voltage signal is at high level and once when the response voltage signal is at low level, the difference is taken as the result, the average value of the difference from a plurality of circles is taken as a final result for improving accuracy, the period of respective sampling at high level equals to the period of respective sampling at low level.

Therefore, comparing with a conventional technology, the present invention has the advantages as follows. First, the impedance detecting circuit adopts units with low voltage and low power consumption and is capable of being powered by a single-supply for applying to being used in a portable electrical impedance imaging system powered by battery. Second, taking the difference between the first sample and the second sample as the demodulating result is capable of further neutralizing the disturbance caused by power frequency and polarized voltage of the electrodes. Last, the average value of the demodulating results is taken as a final result for further improving accuracy.

These and other objectives, features, and advantages of the present invention will become apparent from the following detailed description, the accompanying drawings, and the appended claims.

DETAILED DESCRIPTION OF THE PREFERRED EMBODIMENT

Specific characteristics and properties of the present invention are further illustrated by preferred embodiments and drawings according to the preferred embodiments as follows.

Figure 1:
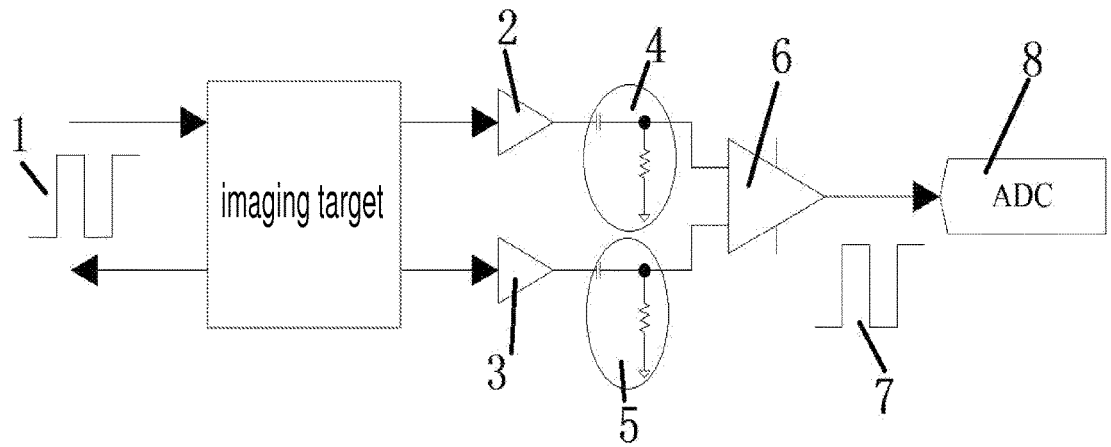
FIG. 1 is a sketch view of an electrical impedance detecting circuit according to a preferred embodiment of the present invention.

Referring to FIG. 1 of the drawings, an electrical impedance detecting device of a portable electrical impedance imaging system according to a preferred embodiment of the present invention is illustrated, comprising:

a pair of exciting electrodes 1 applied on a surface of an imaging target for sending a square wave excitation current signal 1, a first operational amplifier 2 and a second operational amplifier 3 parallel connected to output ports of the pair of exciting electrodes, a first high-pass filter RC circuit 4 connected to an output port of the first operational amplifier 2 and a second high-pass filter RC circuit 5 connected to an output port of the second operational amplifier 3, an A/D circuit 8 connected to a signal output port of the first high-pass filter RC circuit 4 and a signal output port of the second high-pass filter RC circuit 5 respectively through a differential amplifier circuit 6, wherein the constant square wave excitation current signal 1 is used for excitation action, and information of electrical impedance is obtained by calculating and demodulating the difference between a voltage amplitude of the square wave excitation current signal 1 at high level and a voltage amplitude of the square wave excitation current signal 1 at low level.

The preferred embodiment of the present invention also provides a method for detecting electrical impedance, comprising steps of:

sending a square wave excitation current signal 1 to an imaging target through a pair of exciting electrodes 1 for generating a response voltage signal;

sampling the response voltage signal by a pair of detecting electrodes, and then buffering and amplifying the sampled response voltage signal by a first operational amplifier 2 and a second operational amplifier 3 with high input impedance, wherein the input impedance of the operational amplifier is high enough for neutralizing an impedance influence caused by contact between the electrodes and skins;

driving the buffered and amplified response voltage signal through a high-pass filter RC circuit 4 and a second high-pass filter RC circuit 5 for filtering out a disturbance caused by power frequency and polarized voltage of the electrodes;

driving the filtered response voltage signal through a differential amplifier circuit 6 for transforming the response voltage signal sampled by the detecting electrodes to a signal-ended signal and amplifying the single-ended signal; and transforming the amplified single-ended signal to a digital signal by an A/D circuit with high-speed and high accuracy for calculating and obtaining information of the electrical impedance by demodulating.

Figure 2:
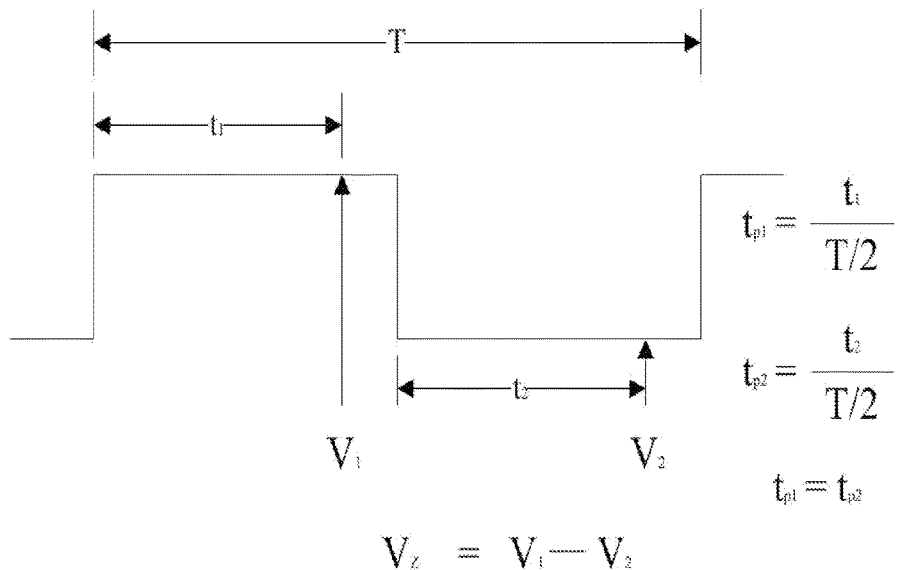
FIG. 2 is a sketch view of a period of respective sampling at high level and a period of respective sampling at low level according to the preferred embodiment of the present invention.

The preferred embodiment of the present invention also provides a method for obtaining information of electrical impedance by demodulating, comprising steps of:

Referring to FIG. 2 of the drawings, sampling a response voltage signal once when the response voltage signal is at high level and once when the response voltage signal is at low level for every circle, and obtaining a first sample $V_1$ and a second sample $V_2$ respectively;

supposing that a period of respective sampling at high level is $$t_{p1} = \frac{t_1}{T/2},$$

wherein $t_1$ is a period between a time of respective sampling at high level and a time of a nearest rising edge of the square wave excitation current signal; correspondingly, supposing that a period of respective sampling at low level is $$t_{p2} = \frac{t_2}{T/2},$$

wherein $t_{p1}=t_{p2}$;

taking values of the period of respective sampling $t_{p1}$ and $t_{p2}$ as 0.8 for common use, wherein the values may be changed for being adaptable to different imaging requirements;

obtaining information of the electrical impedance by calculating and demodulating difference $V_z=V_1-V_2$ between the first sample $V_1$ and the second sample $V_2$; and taking an average value of $V_z$ from a plurality of circles as a final result for improving accuracy.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for detecting electrical impedance, comprising steps of:
    a) sending a square wave excitation current signal to an imaging target through a pair of exciting electrodes for generating a response voltage signal;
    b) buffering and amplifying the sampled response voltage signal by a first operational amplifiers and a second operational amplifiers with high input impedance for neutralizing an impedance influence caused by contact between the electrodes and skins;
    c) driving the buffered and amplified response voltage signal through a first high-pass filter RC circuit and a second high-pass filter RC circuit by the first operational amplifiers and the second operational amplifiers for filtering out a disturbance caused by power frequency and polarized voltage of the electrodes;
    d) driving the filtered response voltage signal through a differential amplifier circuit for transforming the filtered response voltage signal to a signal-ended signal and amplifying the single-ended signal; and
    e) transforming the amplified single-ended signal to a digital signal by an A/D circuit with high-speed and high accuracy for calculating and obtaining information of the electrical impedance by demodulating;
    wherein the response voltage signal is sampled once when the response voltage signal is at high level and once when the response voltage signal is at low level for every circle, and a first sample $V_1$ and a second sample $V_2$ are obtained respectively;
    a period of respective sampling at high level is supposed as $$t_{p1} = \frac{t_1}{T/2},$$

wherein $t_1$ is a period between a time of respective sampling at high level and a time of a nearest rising edge of the square wave excitation current signal; correspondingly, a period of respective sampling at low level is $$t_{p2} = \frac{t_2}{T/2};$$

wherein $t_{p1}=t_{p2}$;
information of the electrical impedance is obtained by calculating and demodulating difference $V_Z=V_1-V_2$ between the first sample $V_1$ and the second sample $V_2$;
an average value of the $V_Z$ from a plurality of the circles is taken as a final result.

2. The method, as recited in claim 1, wherein a response voltage signal is generated by said square wave excitation current signal, detecting electrodes are applied on the imaging target for sampling said response voltage signal.

* * * * *